United States Patent
Lotz et al.

(10) Patent No.: US 12,091,380 B2
(45) Date of Patent: Sep. 17, 2024

(54) PROCESSES FOR PRODUCING POLY ALPHA OLEFINS AND APPARATUSES THEREFOR

(71) Applicant: ExxonMobil Chemical Patents Inc., Baytown, TX (US)

(72) Inventors: Monica D. Lotz, Houston, TX (US); Jennifer L. Rapp, Houston, TX (US); Patrick C. Chen, Houston, TX (US); Md Safatul Islam, Pearland, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 213 days.

(21) Appl. No.: 17/633,918

(22) PCT Filed: Jun. 3, 2020

(86) PCT No.: PCT/US2020/035812
§ 371 (c)(1),
(2) Date: Feb. 8, 2022

(87) PCT Pub. No.: WO2021/029939
PCT Pub. Date: Feb. 18, 2021

(65) Prior Publication Data
US 2022/0289644 A1   Sep. 15, 2022

Related U.S. Application Data

(60) Provisional application No. 62/885,014, filed on Aug. 9, 2019.

(30) Foreign Application Priority Data

Oct. 24, 2019   (EP) .................................. 19205051

(51) Int. Cl.
C07C 5/25 (2006.01)
C07C 2/34 (2006.01)
C10M 177/00 (2006.01)

(52) U.S. Cl.
CPC .................. *C07C 5/25* (2013.01); *C07C 2/34* (2013.01); *C10M 177/00* (2013.01);
(Continued)

(58) Field of Classification Search
CPC ......... C07C 5/25; C07C 2/34; C07C 2531/14; C07C 2531/22; C07C 2531/10;
(Continued)

(56) References Cited

U.S. PATENT DOCUMENTS 3,852,207 A   12/1974   Stangeland et al.
3,904,513 A   9/1975   Fischer et al.
(Continued)

FOREIGN PATENT DOCUMENTS

EP   0426638 A3   8/1991
WO   97/22635 A1   6/1997
(Continued)

OTHER PUBLICATIONS

Extended European Search Report received for European Patent Application No. 19205051.6 mailed on Apr. 8, 2020, 7 Pages.
(Continued)

*Primary Examiner* — Ali Z Fadhel (57) ABSTRACT

The present disclosure provides processes and apparatus for producing poly alpha olefins. In at least one embodiment, a process to produce a poly alpha olefin includes introducing a first olefin monomer to a first catalyst and an activator in a first reactor to form a first reactor effluent comprising olefin dimers and olefin timers. The process includes heating the first reactor effluent to form an isomerized product and introducing the isomerized product to a filtration unit to
(Continued)

form a filtration effluent. The process may include introducing the filtration effluent to a first distillation unit to form a first distillation effluent. The process may include introducing the first distillation effluent to a second distillation unit to form a second distillation effluent. The process includes introducing the first distillation effluent and/or the second distillation effluent to a second catalyst in a second reactor to form a second reactor effluent comprising the olefin timers.

17 Claims, 2 Drawing Sheets

(52) U.S. Cl.
CPC ...... *C07C 2531/14* (2013.01); *C07C 2531/22* (2013.01); *C10M 2205/0285* (2013.01)

(58) Field of Classification Search
CPC ............... C07C 7/04; C10M 177/00; C10M 2205/0285; B01D 3/009; B01D 3/143
See application file for complete search history.

(56) References Cited

U.S. PATENT DOCUMENTS

| | | | |
|---|---|---|---|
| 4,125,569 A | 11/1978 | Jackson | |
| 4,157,294 A | 6/1979 | Iwao et al. | |
| 4,673,487 A | 6/1987 | Miller | |
| 5,241,025 A | 8/1993 | Hlatky et al. | |
| 5,284,988 A | 2/1994 | Schaerl, Jr. et al. | |
| 5,447,895 A | 9/1995 | Marks et al. | |
| 6,548,724 B2 | 4/2003 | Bagheri et al. | |
| 7,511,104 B2 | 3/2009 | Pehlert et al. | |
| 9,365,788 B2 | 6/2016 | Emett et al. | |
| 9,708,549 B2 | 7/2017 | Gee et al. | |
| 9,745,230 B2 | 8/2017 | Small et al. | |
| 2007/0043248 A1 | 2/2007 | Wu et al. | |
| 2009/0156874 A1 | 6/2009 | Patil et al. | |
| 2009/0240012 A1 | 9/2009 | Patil et al. | |
| 2010/0292420 A1 | 11/2010 | Fushimi et al. | |
| 2010/0292424 A1 | 11/2010 | Wu et al. | |
| 2011/0137091 A1 | 6/2011 | Yang et al. | |
| 2013/0090277 A1 | 4/2013 | Martin et al. | |
| 2013/0130952 A1 | 5/2013 | Luo et al. | |
| 2013/0245343 A1* | 9/2013 | Emett | C10M 143/08 585/530 |
| 2014/0275664 A1* | 9/2014 | Yang | C10M 107/10 585/18 |

FOREIGN PATENT DOCUMENTS

| | | |
|---|---|---|
| WO | 2007/011973 A1 | 1/2007 |
| WO | 2007144474 A1 | 12/2007 |
| WO | 2012/134688 A1 | 10/2012 |
| WO | 2021/029939 A1 | 2/2021 |

OTHER PUBLICATIONS

International Preliminary Report on Patentability received for PCT Application No. PCT/US2020/035812, mailed on Feb. 17, 2022, 7 Pages.

International Search Report and Written Opinion received for PCT Application No. PCT/US2020/035812, mailed on Sep. 1, 2020, 8 Pages.

* cited by examiner

FIG. 5

PROCESSES FOR PRODUCING POLY ALPHA OLEFINS AND APPARATUSES THEREFOR

CROSS-REFERENCE TO RELATED APPLICATION

This application is a National Phase Application claiming priority to PCT Application Ser. No. PCT/US2020/035812 filed Jun. 3, 2020, which claims the benefit of U.S. Provisional Application 62/885014 filed Aug. 9, 2019 entitled "Processes for Producing Poly Alpha Olefins and Apparatuses Thereof", the entirety of which is incorporated by reference herein.

This application is related to U.S. Ser. No. 62/884,991, (2019EM298) entitled "Processes for Producing Poly Alpha Olefins and Method of Analysis and Apparatuses Thereof," filed Aug. 9, 2019.

FIELD

The present disclosure provides processes and apparatuses for producing poly alpha olefins.

BACKGROUND

Efforts to improve the performance of lubricant basestocks by the oligomerization of hydrocarbon fluids have been ongoing in the petroleum industry for over fifty years. These efforts have led to the market introduction of a number of synthetic lubricant basestocks. Much of the research involving synthetic lubricant basestocks has been toward developing fluids that exhibit useful viscosities over a wide temperature range while also maintaining lubricities, thermal and oxidative stabilities, and pour points equal to or better than those for mineral lubricants.

The viscosity-temperature relationship of a lubricant is one criterion that can be considered when selecting a lubricant for a particular application. The viscosity index (VI) is an empirical number which indicates the rate of change in the viscosity of an oil within a given temperature range. A high VI oil will thin out at elevated temperatures slower than a low VI oil. In most lubricant applications, a high VI oil is desirable because maintaining a higher viscosity at higher temperatures translates into better lubrication.

Poly alpha olefins (PAOs) are a class of materials that are exceptionally useful as high performance synthetic lubricant basestocks. PAOs possess excellent flow properties at low temperatures, good thermal and oxidative stability, low evaporation losses at high temperatures, high viscosity index, good friction behavior, good hydrolytic stability, and good erosion resistance. PAOs are miscible with mineral oils, other synthetic hydrocarbon liquids, fluids and esters. Consequently, PAOs are suitable for use in engine oils, compressor oils, hydraulic oils, gear oils, greases, and functional fluids.

Although most of the research on metallocene-based PAOs has focused on higher viscosity oils, recent research has looked at producing low viscosity PAOs for automotive applications. A current trend in the automotive industry is toward extending oil drain intervals and improving fuel economy. This trend is driving increasingly stringent performance requirements for lubricants. New PAOs with improved properties such as high viscosity index, low pour point, high shear stability, improved wear performance, increased thermal and oxidative stability, and/or wider viscosity ranges are needed to meet these new performance requirements. New methods to produce such PAOs are also needed.

US 2007/0043248 discloses a process using a metallocene catalyst for the production of low viscosity (4 to 10 cSt) PAO basestocks. This technology is attractive because the metallocene-based low viscosity PAO has excellent lubricant properties. One disadvantage of the low viscosity metallocene-catalyzed process is that a significant amount of dimer is formed. This dimer is typically not useful as a lubricant basestock because it has very poor low temperature and volatility properties. Recent industry research has looked at recycling the dimer portion formed in the metallocene-catalyzed process into a subsequent oligomerization process. However, recycling the dimer portion into a subsequent oligomerization process is selective for only certain dimeric structures of the recycled feed. In addition, multiple oligomerization processes have low throughput and low overall yield of product(s) due to complex reactor setups, such as reactors having cellulosic body feed-type filtration units which slow throughput due to slow flow rates of feed through the filtration unit.

There is a need for improved processes and apparatuses for producing poly alpha olefins, such as low viscosity poly alpha olefins.

References for citing in an Information Disclosure Statement (37 CFR 1.97(h)): U.S. Pat. Nos. 9,365,788; 6,548,724; 5,284,988; US Patent Publication Nos. 2013/0090277; 2007/0043248; 2013/0130952; PCT Publication No. WO 2012/134688.

SUMMARY

In at least one embodiment, a process to produce a poly alpha olefin includes introducing a first olefin monomer to a first catalyst and an activator in a first reactor to form a first reactor effluent comprising olefin dimers and olefin trimers. The process includes heating the first reactor effluent to form an isomerized product and introducing the isomerized product to a filtration unit to form a filtration effluent. The process includes introducing the filtration effluent to a first distillation unit to form a first distillation effluent. The process includes introducing the first distillation effluent to a second distillation unit to form a second distillation effluent. The process includes introducing the second distillation effluent to a second catalyst in a second reactor to form a second reactor effluent comprising the olefin trimers.

In at least one embodiment, a process to produce a poly alpha olefin includes introducing a first olefin monomer to a first catalyst and an activator in a first reactor to form a first reactor effluent comprising olefin dimers and olefin trimers. The process includes introducing the first reactor effluent to a first distillation unit to form a first distillation effluent. The process includes introducing the first distillation effluent to a second distillation unit to form a second distillation effluent and heating the second distillation effluent to form an isomerized product. The process includes introducing the isomerized product to a second catalyst in a second reactor to form a second reactor effluent comprising the olefin trimers.

In at least one embodiment, a process to produce a poly alpha olefin includes introducing a first olefin monomer to a first catalyst and an activator in a first reactor to form a first reactor effluent comprising olefin dimers and olefin trimers. The process includes introducing the first reactor effluent to a first distillation unit to form a first distillation effluent. The process includes introducing the first distillation effluent to a second distillation unit to form a second distillation effluent and introducing the second distillation effluent to a second catalyst in a second reactor to form a second reactor effluent comprising the olefin trimers.

In at least one embodiment, an apparatus includes a first reactor coupled at a first end with a first end of a first distillation unit. The apparatus includes a second distillation unit coupled with (1) a second end of the first distillation unit at a first end of the second distillation unit, (2) a first end of a second reactor at a second end of the second distillation unit via a line, and (3) a first end of a hydrogenation unit at a third end of the second distillation unit.

In at least one embodiment, an apparatus includes a first reactor coupled at a first end with a first end of a filtration unit. The apparatus includes a first distillation unit coupled at a first end with a second end of the filtration unit. The apparatus includes a second distillation unit coupled with (1) a second end of the first distillation unit at a first end of the second distillation unit, (2) a first end of a second reactor at a second end of the second distillation unit via a line, and (3) a first end of a hydrogenation unit at a third end of the second distillation unit.

BRIEF DESCRIPTION OF THE DRAWINGS

So that the manner in which the above recited features of the present disclosure can be understood in detail, a more particular description of the disclosure, briefly summarized above, may be had by reference to examples, some of which are illustrated in the appended drawings. It is to be noted, however, that the appended drawings illustrate only typical examples of this present disclosure and are therefore not to be considered limiting of its scope, for the present disclosure may admit to other equally effective examples.

To facilitate understanding, identical reference numerals have been used, where possible, to designate identical elements that are common to the figures. It is contemplated that elements and features of one example may be beneficially incorporated in other examples without further recitation.

DETAILED DESCRIPTION

The present disclosure provides processes and apparatuses for producing poly alpha olefins. In at least one embodiment, a process includes oligomerizing linear alpha olefins to form vinylidene dimers. The process includes isomerizing the vinylidene dimers to form tri-substituted olefin dimers, and oligomerizing the tri-substituted olefin dimers to form trimers. Tri-substituted olefin dimers provide higher selectivity (than vinylidene dimers) to trimers in an oligomerization process. Isomerization of vinylidene dimers to tri-substituted olefin dimers provides higher overall yields of trimers. The process can further include hydrogenating the trimers to form saturated trimers.

It has been discovered that vinylidene dimers can be isomerized in the absence of added isomerization catalyst, rendering isomerization in an additional reactor merely optional. A heat exchanger can be coupled with a line transporting the vinylidene dimers from a first reactor (such as a reactor configured to oligomerize linear alpha olefins to form vinylidene dimers) to a filtration unit and/or to a distillation unit. Additionally or alternatively, a heat exchanger can be coupled with a line transporting vinylidene dimers from a distillation unit to a second reactor (such as a reactor configured to oligomerized tri-substituted olefin dimers to form trimers). Isomerizing vinylidene dimers in the absence of an added isomerization catalyst (and/or in the absence of an isomerization reactor) provides substantial cost savings and throughput enhancement as compared to conventional poly alpha olefin processes. Furthermore, isomerizing vinylidene dimers in the absence of an added isomerization catalyst renders merely optional a filtration unit coupled with the first reactor. However, filtration is typically used to filter particulates. Additionally or alternatively, a less expensive and less complex filtration unit can be used (such as a crude particulate filter having a large pore size) instead of a conventional cellulosic body feed-type filtration unit, which provides additional cost savings and throughput enhancement.

When used in the present disclosure, in accordance with conventional terminology in the art, the following terms are defined for the sake of clarity. The term "vinyl" is used to designate groups of formula $RCH=CH_2$. The term "vinylidene" is used to designate groups of formula $RR'=CH_2$. The term "disubstituted vinylene" is used to designate groups of formula $RCH=CHR'$. The term "tri-substituted vinylene" is used to designate groups of formula $RR'C=CHR''$. The term "tetrasubstituted vinylene" is used to designate groups of formula $RR'C=CR''R'''$. For all of these formulas, R, R', R", and R''' are alkyl groups which may be identical or different from each other.

The monomer feed used in both the first oligomerization and optionally contacted with the recycled intermediate PAO dimer and light olefin fractions in the subsequent oligomerization is at least one linear alpha olefin (LAO). The LAO may be comprised of monomers of 6 to 24 carbon atoms, usually 6 to 20, such as 6 to 14 carbon atoms, such as 1-hexene, 1-octene, 1-nonene, 1-decene, 1-dodecene, and 1-tetradecene. Olefins with even carbon numbers can be the LAO used. Additionally, the olefins can be treated to remove catalyst poisons, such as peroxides, oxygen, sulfur, nitrogen-containing organic compounds, and/or acetylenic compounds as described in WO 2007/011973.

For the purposes of the present disclosure, the numbering scheme for the Periodic Table Groups is used as described in *Chemical and Engineering News*, v. 63 (5), pg. 27 (1985). Therefore, a "Group 8 metal" is an element from Group 8 of the Periodic Table, e.g., Fe.

First Oligomerization

Catalyst

Useful catalysts in the first oligomerization include single site catalysts. For example, the first oligomerization can utilize a metallocene catalyst. In this disclosure, the terms "metallocene catalyst" and "transition metal compound" are used interchangeably. Catalysts can give high catalyst productivity and result in a product having low viscosity and low molecular weight. Metallocene catalysts may be bridged or unbridged and substituted or unsubstituted. They may have leaving groups including dihalides or dialkyls. When the leaving groups are dihalides, tri-alkylaluminum may be used to promote the reaction. In general, useful transition metal compounds may be represented by the following formula:

$$X^1X^2M^1(CpCp^*)M^2X^3X^4$$

wherein:

$M^1$ is an optional bridging element, such as selected from silicon or carbon;

$M^2$ is a Group 4 metal;

each of Cp and Cp* are the same or different substituted or unsubstituted cyclopentadienyl ligand systems wherein, if substituted, the substitutions may be independent or linked to form multicyclic structures;

each of $X^1$ and $X^2$ is independently hydrogen, hydride radicals, hydrocarbyl radicals, substituted hydrocarbyl radicals, silylcarbyl radicals, substituted silylcarbyl radicals, germylcarbyl radicals, or substituted germylcarbyl radicals or are independently selected from hydrogen, branched or unbranched $C_1$ to $C_{20}$ hydrocarbyl radicals, or branched or unbranched substituted $C_1$ to $C_{20}$ hydrocarbyl radicals; and each of $X^3$ and $X^4$ is independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, substituted germylcarbyl radicals, or $X^3$ and $X^4$ are joined and bound to the metal atom to form a metallacycle ring containing from about 3 to about 20 carbon atoms, or are independently selected from hydrogen, branched or unbranched $C_1$ to $C_{20}$ hydrocarbyl radicals, or branched or unbranched substituted $C_1$ to $C_{20}$ hydrocarbyl radicals.

For this disclosure, a hydrocarbyl radical is a $C_1$-$C_{100}$ radical and may be linear, branched, or cyclic. In at least one embodiment, a substituted hydrocarbyl radical includes halocarbyl radicals, substituted halocarbyl radicals, silylcarbyl radicals, and germylcarbyl radicals.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$—, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SPR^*_2$, $SR^*$, $BR^*_2$, $SiR^*_3$, $GeR^*_3$, $SnR^*_3$, $PbR^*_3$, or where at least one non-carbon atom or group has been inserted within the halocarbyl radical such as —O—, —S—, —Se—, —Te—, —N(R*)—, =N—, —P(R*)—, =P—, —As(R*)—, =As—, —Sb (R*)—, =Sb—, —B(R*)—, =B—, —Si(R*)$_2$—, —Ge (R*)$_2$—, —Sn(R*)$_2$—, —Pb(R*)$_2$—, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^*_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, where R* is independently a hydrocarbyl or halocarbyl radical and two or more R* may join together to form a substituted or unsubstituted saturated, partially unsaturated or aromatic cyclic or polycyclic ring structure.

In at least one embodiment, the transition metal compound may be represented by the following formula:

$$X^1X^2M^1(CpCp^*)M^2X^3X^4$$

wherein:

$M^1$ is a bridging element, such as silicon;

$M^2$ is a Group 4 metal, such as titanium, zirconium or hafnium;

Cp and Cp* are the same or different substituted or unsubstituted indenyl or tetrahydroindenyl rings that are each bonded to both $M^1$ and $M^2$;

$X^1$ and $X^2$ are independently hydrogen, hydride radicals, hydrocarbyl radicals, substituted hydrocarbyl radicals, silylcarbyl radicals, substituted silylcarbyl radicals, germylcarbyl radicals, or substituted germylcarbyl radicals; and $X^3$ and $X^4$ are independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both $X^3$ and $X^4$ are joined and bound to the metal atom to form a metallacycle ring containing from about 3 to about 20 carbon atoms.

In using the terms "substituted or unsubstituted tetrahydroindenyl," "substituted or unsubstituted tetrahydroindenyl ligand," the substitution to the aforementioned ligand may be hydrocarbyl, substituted hydrocarbyl, halocarbyl, substituted halocarbyl, silylcarbyl, or germylcarbyl. The substitution may also be within the ring giving heteroindenyl ligands or heterotetrahydroindenyl ligands, either of which can additionally be substituted or unsubstituted.

In another embodiment, useful transition metal compounds may be represented by the following formula:

$$L^AL^BL^C_1MDE$$

wherein:

$L^A$ is a substituted cyclopentadienyl or heterocyclopentadienyl ancillary ligand π-bonded to M;

$L^B$ is a member of the class of ancillary ligands recited for $L^A$, or is J, wherein J is a heteroatom ancillary ligand σ-bonded to M; the $L^A$ and $L^B$ ligands may be covalently bridged together through a Group 14 element linking group;

$L^C_1$ is an optional neutral, non-oxidizing ligand having a dative bond to M (i equals 0 to 3);

M is a Group 4 or 5 transition metal; and

D and E are independently monoanionic labile ligands, each having a π-bond to M, optionally bridged to each other or $L^A$ or $L^B$. The mono-anionic ligands are displaceable by a suitable activator to permit insertion of a polymerizable monomer or a macromonomer can insert for coordination polymerization on the vacant coordination site of the transition metal compound.

In at least one embodiment, an oligomerization process utilizes a highly active metallocene catalyst. For example, the catalyst productivity may be greater than about 15,000 g PAO/g catalyst, such as greater than about 20,000 g PAO g catalyst, such as greater than about 25,000 g PAO/g catalyst, such as greater than about 30,000 g PAO g catalyst, wherein g PAO/g catalyst represents grams of PAO formed per grams of catalyst used in the oligomerization reaction.

High productivity rates are also achieved. In at least one embodiment, the productivity rate in the first oligomerization is greater than about 4,000 g PAO/g catalyst*hour (also referred to as "gPAO/g catalyst/h"), such as greater than about 6,000 g PAO/g catalyst*hour, such as greater than about 8,000 g PAO/g catalyst*hour, such as greater than about 10,000 g PAO g catalyst*hour, wherein g PAO/g catalyst represents grams of PAO formed per grams of catalyst used in the oligomerization reaction.

Activator

The catalyst may be activated by any suitable activator such as a non-coordinating anion (NCA) activator. An NCA is an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the NCA. Suitable metals include aluminum, gold, and platinum. Suitable metalloids include boron, aluminum, phosphorus, and silicon.

Lewis acid and ionic activators may also be used. Useful but non-limiting examples of Lewis acid activators include triphenylboron, tris-perfluorophenylboron, and tris-perfluorophenylaluminum. Useful but non-limiting examples of ionic activators include dimethylanilinium tetrakisperfluorophenylborate, triphenylcarbenium tetrakisperfluorophenylborate, and dimethylanilinium tetrakisperfluorophenylaluminate.

An additional subclass of useful NCAs comprises stoichiometric activators, which can be either neutral or ionic. Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy, and halides. For example, the three groups can be independently selected from halogen, mono or multicyclic (including halosubstituted) aryls, alkyls, and alkenyl compounds and mixtures thereof, for example alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). For example, the three groups can be alkyls having 1 to 4 carbon groups, phenyl, naphthyl, or mixtures thereof. For example, the three groups are halogenated, such as fluorinated, aryl groups. Ionic stoichiometric activator compounds may contain an active proton, or some other cation associated with, but not coordinated to, or only loosely coordinated to, the remaining ion of the ionizing compound.

Ionic catalysts can be prepared by reacting a transition metal compound with an activator, such as $B(C_6F_6)_3$, which upon reaction with the hydrolyzable ligand (X') of the transition metal compound forms an anion, such as ([B$(C_6F_5)_3$(X')]$^-$)([B$(C_6F_5)_3$(X')]$^-$), which stabilizes the cationic transition metal species generated by the reaction. The catalysts can be prepared with activator components which are ionic compounds or compositions. Additionally or alternatively, activators can be prepared utilizing neutral compounds.

Compounds used as an activator component in the preparation of the ionic catalyst systems used in a process of the present disclosure can include a cation, which can be a Brønsted acid capable of donating a proton, and a compatible NCA which anion is relatively large (bulky), capable of stabilizing the active catalyst species which is formed when the two compounds are combined and said anion will be sufficiently labile to be displaced by olefinic, diolefinic, and acetylenically unsaturated substrates or other neutral Lewis bases such as ethers or nitriles.

In at least one embodiment, the ionic stoichiometric activators include a cation and an anion component, and may be represented by the following formula:

wherein:

L** is an neutral Lewis base;

H is hydrogen;

(L**–H)$^+$ is a Brønsted acid or a reducible Lewis acid; and $A^{d-}$ is an NCA having the charge d–, and d is an integer from 1 to 3.

The cation component, (L**–H)$_d^+$ may include Brønsted acids such as protons or protonated Lewis bases or reducible Lewis acids capable of protonating or abstracting a moiety, such as an alkyl or aryl, from the catalyst after alkylation.

The activating cation (L–H)$_d^+$ may be a Brønsted acid, capable of donating a proton to the alkylated transition metal catalytic precursor resulting in a transition metal cation, including ammoniums, oxoniums, phosphoniums, silyliums, and mixtures thereof, such as ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L–H)$_d^+$ may also be a moiety such as silver, tropylium, carbeniums, ferroceniums and mixtures, such as carbeniums and ferroceniums; such as triphenyl carbenium. The anion component $A_d^-$ includes those having the formula [Mk+Qn]$_d^-$ wherein k is an integer from 1 to 3; n is an integer from 2-6; n–k=d; M is an element selected from Group 13 of the Periodic Table of the Elements, such as boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. For example, each Q is a fluorinated hydrocarbyl group having 1 to 20 carbon atoms, such as each Q is a fluorinated aryl group, such as each Q is a pentafluoryl aryl group. Examples of suitable $A_d^-$ also include diboron compounds as disclosed in U.S. Pat. No. 5,447,895, which is incorporated herein by reference.

Boron compounds which may be used as an NCA activator in combination with a co-activator are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl) ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium)tetrakis(3,5-bis(trifluoromethyl)phenyl)borate.

In at least one embodiment, the NCA activator, $(L^{**}-H)_d^+(A_d^-)$, is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Pehlert et al., U.S. Pat. No. 7,511,104 provides additional details on NCA activators that may be useful, and these details are hereby incorporated by reference.

Additional activators that may be used include alumoxanes or alumoxanes in combination with an NCA. In one embodiment, alumoxane activators are utilized as an activator. Alumoxanes are generally oligomeric compounds containing —Al($R^1$)-O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used.

A catalyst co-activator is a compound capable of alkylating the catalyst, such that when used in combination with an activator, an active catalyst is formed. Co-activators may include alumoxanes such as methylalumoxane, modified alumoxanes such as modified methylalumoxane, and aluminum alkyls such trimethylaluminum, tri-isobutylaluminum, triethylaluminum, tri-isopropylaluminum, tri-n-hexylaluminum, tri-n-octylaluminum, tri-n-decylaluminum, and tri-n-dodecylaluminum. Co-activators are typically used in combination with Lewis acid activators and ionic activators when the catalyst is not a dihydrocarbyl or dihydride complex.

The co-activator may also be used as a scavenger to deactivate impurities in feed or reactors. A scavenger is a compound that is sufficiently Lewis acidic to coordinate with polar contaminates and impurities adventitiously occurring in the polymerization feedstocks or reaction medium. Such impurities can be inadvertently introduced with any of the reaction components, and adversely affect catalyst activity and stability. Scavenging compounds may be organometallic compounds such as triethyl aluminum, triethyl borane, tri-isobutyl aluminum, methylalumoxane, isobutyl aluminumoxane, tri-n-hexyl aluminum, tri-n-octyl aluminum, and those having bulky substituents covalently bound to the metal or metalloid center being exemplary to minimize adverse interaction with the active catalyst. Other useful scavenger compounds may include those mentioned in U.S. Pat. No. 5,241,025; EP-A 0426638; and WO 1997/022635, which are hereby incorporated by reference for such details.

The reaction time or reactor residence time can be dependent on the type of catalyst used, the amount of catalyst used, and the desired conversion level. Different transition metal compounds (also referred to as metallocene) have different activities. A high amount of catalyst loading tends to give high conversion at short reaction time. However, a high amount of catalyst usage can make the production process uneconomical and difficult to manage the reaction heat or to control the reaction temperature. Therefore, it is useful to choose a catalyst with maximum catalyst productivity to minimize the amount of metallocene and the amount of activators needed. For a catalyst system of metallocene plus a Lewis Acid or an ionic promoter with NCA component, the transition metal compound used may be from 0.01 microgram to 500 micrograms of metallocene component/gram of alpha-olefin feed, such as from 0.1 microgram to 100 microgram of metallocene component per gram of alpha-olefin feed. Furthermore, the molar ratio of the NCA activator to metallocene can be from 0.1 to 10, such as 0.5 to 5, such as 0.5 to 3. For the co-activators of alkylaluminums, the molar ratio of the co-activator to metallocene can be from 1 to 1,000, such as 2 to 500, such as 4 to 400.

In selecting oligomerization conditions, to obtain the desired first reactor effluent, the system uses the transition metal compound (also referred to as the catalyst), activator, and co-activator. US 2007/043248 and US 2010/029242 provide additional details of metallocene catalysts, activators, co-activators, and appropriate ratios of such compounds in the feedstock that may be useful, and these additional details are hereby incorporated by reference.

First Oligomerization Process Conditions

Many oligomerization processes and reactor types used for single site- or metallocene-catalyzed oligomerizations such as solution, slurry, and bulk oligomerization processes may be used for the first oligomerization. In some embodiments, if a solid catalyst is used, a slurry or continuous fixed bed or plug flow process is suitable. In at least one embodiment, the monomers can be contacted with the metallocene compound and the activator in the solution phase, bulk phase, or slurry phase, such as in a continuous stirred tank reactor or a continuous tubular reactor. In at least one embodiment, the temperature in any reactor used herein is from about −10° C. to about 250° C., such as from about 30° C. to about 220° C., such as from about 50° C. to about 180° C., such as from about 80° C. to about 150° C. In at least one embodiment, the pressure in any reactor used herein is from about 10.13 to about 10132.5 kPa (0.1 to 100 atm/1.5 to 1,500 psi), such as from about 50.66 to about 7,600 kPa (0.5 to 75 atm/8 to 1,125 psi), such as from about 101.3 to about 5,066.25 kPa (1 to 50 atm/15 to 750 psi). In another embodiment, the pressure in any reactor used herein is from about 101.3 to about 5,066,250 kPa (1 to 50,000 atm), such as about 101.3 to about 2,533,125 kPa (1 to 25,000 atm). In at least one embodiment, the residence time in any reactor is from about 1 second to about 100 hours, such as about 30 seconds to about 50 hours, such as about 2 minutes to about 6 hours, such as about 1 to about 6 hours. In another embodiment, solvent or diluent is present in the reactor. These solvents or diluents are usually pre-treated in same manners as the feed olefins.

The oligomerization can be run in batch mode, where all the components are added into a reactor and allowed to react to a degree of conversion, either partial or full conversion. Subsequently, the catalyst is deactivated by any suitable means, such as exposure to air or water, or by addition of alcohols or solvents containing deactivating agents. The oligomerization can also be carried out in a semi-continuous operation, where feeds and catalyst system components are continuously and simultaneously added to the reactor so as to maintain a constant ratio of catalyst system components to feed olefin(s). When all feeds and catalyst components are added, the reaction is allowed to proceed to a pre-determined stage. The reaction is then discontinued by catalyst deactivation in the same manner as described for batch operation. The oligomerization can also be carried out in a continuous operation, where feeds and catalyst system components are continuously and simultaneously added to the reactor so to maintain a constant ratio of catalyst system and feeds. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. In at least one embodiment, any of the processes to prepare PAOs described herein are continuous processes.

A production facility may have one single reactor or several reactors arranged in series or in parallel, or both, to maximize productivity, product properties, and general process efficiency. The catalyst, activator, and co-activator may be delivered as a solution or slurry in a solvent or in the LAO feed stream, either separately to the reactor, activated in-line just prior to the reactor, or pre-activated and pumped as an activated solution or slurry to the reactor. Oligomerizations are carried out in either single reactor operation, in which the monomer, or several monomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to the first reactor and another component to other reactors.

The reactors and associated equipment are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds. Additionally, in one embodiment of any of the processes described herein, the feed olefins and/or solvents are treated to remove catalyst poisons, such as peroxides, oxygen or nitrogen-containing organic compounds or acetylenic compounds. Such treatment will increase catalyst productivity 2- to 10-fold or more.

The reaction time or reactor residence time is usually dependent on the type of catalyst used, the amount of catalyst used, and the desired conversion level. When the catalyst is a metallocene, different metallocenes have different activities. Usually, a higher degree of alkyl substitution on the cyclopentadienyl ring, or bridging improves catalyst productivity. High catalyst loading tends to give high conversion in short reaction time. However, high catalyst usage can make the process uneconomical and difficult to manage the reaction heat or to control the reaction temperature. Therefore, it is useful to choose a catalyst with high catalyst productivity to minimize the amount of metallocene and the amount of activators needed.

US 2007/043248 and US 2010/292424 provide additional details on acceptable oligomerization processes using metallocene catalysts, and the details of these processes, process conditions, catalysts, activators, and co-activators are hereby incorporated by reference to the extent that they are not inconsistent with anything described in this disclosure.

Due to the low activity of some metallocene catalysts at high temperatures, low viscosity PAOs are typically oligomerized in the presence of added hydrogen at lower temperatures. An advantage is that hydrogen acts as a chain terminator, effectively decreasing molecular weight and viscosity of the PAO. Hydrogen can also hydrogenate the olefin, however, saturating the LAO feedstock and PAO, which would prevent LAO or PAO dimer from being usefully recycled into a further oligomerization process. Thus it is an improvement to be able to make an intermediate PAO without having to add hydrogen for chain termination such that the unreacted LAO feedstock and intermediate PAO dimer maintain their unsaturation, and thus their reactivity, for a subsequent recycle process.

The intermediate PAO produced can be a mixture of dimers (such as vinylidene dimers), trimers, and optionally tetramer and higher oligomers of the respective alpha olefin feedstocks. This intermediate PAO and portions thereof is referred to interchangeably as the "first reactor effluent" from which unreacted monomers have optionally been removed.

The intermediate PAO dimer portion can have a number average molecular weight from about 120 g/mol to about 600 g/mol.

The intermediate PAO dimer portion can possess at least one carbon-carbon unsaturated double bond. A portion of this intermediate PAO dimer can include tri-substituted vinylene. The tri-substituted vinylene can have possible isomer structures that may coexist and differ regarding where the unsaturated double bond is located, as represented by the following structure:

wherein the dashed line represents the two possible locations where the unsaturated double bond may be located and $R^x$ and $R^y$ are independently selected from a $C_3$ to $C_{21}$ alkyl group, such as from linear $C_3$ to $C_{21}$ alkyl group. Although the cis-form of tri-substituted vinylene is shown above, the trans-form of tri-substituted vinylene is also contemplated for one or more embodiments of the present disclosure. In at least one embodiment, the tri-substituted vinylenes of a feed are predominantly of the trans-isomer.

In at least one embodiment, the intermediate PAO dimer contains greater than about 20 wt %, such as greater than about 25 wt %, such as greater than about 30 wt %, such as greater than about 40 wt %, such as greater than about 50 wt %, such as greater than about 60 wt %, such as greater than about 70 wt %, such as greater than about 80 wt % of tri-substituted vinylene dimer represented by the general structure above.

In at least one embodiment, Rx and Ry are independently $C_3$ to $C_{11}$ alkyl groups. In at least one embodiment, $R^x$ and $R^y$ are both $C_2$. In at least one embodiment, the intermediate PAO dimer comprises a portion of tri-substituted vinylene dimer that is represented by the following structure:

wherein the dashed line represents the two possible locations where the unsaturated double bond may be located.

In at least one embodiment, the intermediate PAO contains less than about 90 wt %, such as less than about 70 wt %, such as less than about 60 wt %, such as less than about 50 wt %, such as less than about 40 wt %, such as less than about 30 weight %, such as less than about 20 wt % of di-substituted vinylidene represented by the formula:

$$R^qR^zC=CH_2$$

wherein $R^q$ and $R^z$ are independently selected from alkyl groups, such as linear alkyl groups, such as $C_3$ to $C_{21}$ linear alkyl groups.

In at least one embodiment, the intermediate PAO product has a kinematic viscosity at 100° C. (KV100) of less than 20 cSt, such as less than 15 cSt, such as less than 12 cSt, such as less than 10 cSt, as determined by ASTM D445. The intermediate PAO trimer portion (after a hydrogenation process) can have a KV100 of less than 4 cSt, such as less than 3.6 cSt. In at least one embodiment, the tetramers and higher oligomer portion of the intermediate PAO (after a hydrogenation process) has a KV100 of less than 30 cSt. In at least one embodiment, the intermediate PAO oligomer portion remaining after the intermediate PAO dimer portion has a KV100 of less than 25 cSt.

The intermediate PAO trimer portion can have a viscosity index (VI) of greater than 125, such as greater than 130, as determined by ASTM D2270. In at least one embodiment, the trimer and higher oligomer portion of the intermediate PAO has a VI of greater than 130, such as greater than 135. In at least one embodiment, the tetramer and higher oligomer portion of the intermediate PAO has a VI of greater than 150, such as greater than 155.

The intermediate PAO trimer portion can have a Noack volatility that is less than 15 wt %, such as less than 14 wt %, such as less than 13 wt %, such as less than 12 wt %, as determined by ASTM D5800. In at least one embodiment, the intermediate PAO tetramers and higher oligomer portion has a Noack volatility that is less than 8 wt %, such as less than 7 wt %, such as less than 6 wt %.

In at least one embodiment, the dimer portion of the intermediate PAO may be a reactor effluent that is sent for further processing, such as that described below.

First Isomerization

Distinct from the oligomerization step described above, after the olefin monomers are oligomerized, the resulting PAO intermediate (comprising vinylidene dimers) may be subjected to isomerization to form an isomerized product (comprising tri-substituted olefin dimers, e.g., tri-substituted vinylene dimers).

It has been discovered that vinylidene dimers (of the PAO intermediate) can be isomerized in the absence of added isomerization catalyst, rendering isomerization in an additional reactor merely optional. A heat exchanger can be coupled with a line transporting the PAO intermediate (comprising vinylidene dimers) from a first reactor to a filtration unit and/or to a distillation unit. The heat exchanger can provide heat to the PAO intermediate to promote isomerization of vinylidene dimers as they flow through the line transporting the PAO intermediate to form an isomerized product that is transferred through the line to the filtration unit and/or the distillation unit. Isomerizing vinylidene dimers in the absence of added isomerization catalyst (and/or in the absence of an isomerization reactor) provides substantial cost savings and throughput enhancement as compared to conventional poly alpha olefin processes. Furthermore, isomerizing vinylidene dimers in the absence of added isomerization catalyst renders merely optional a filtration unit coupled with the first reactor, as described in more detail below.

Isomerization is distinct from the oligomerization as the isomerization reaction does not result in two or more of the individual monomers or polymers bonding together, but is instead a rearrangement of the structure of the product; e.g., movement of double bonds or branching locations of the product.

In at least one embodiment, the isomerized product contains greater than 50 wt % of tri-substituted vinylene dimer represented by the general structure above, such as greater than 55 wt %, such as greater than 60 wt %, such as greater than 65 wt %, such as greater than 75 wt %, such as greater than 85 wt %, such as greater than 90 wt %, such as greater than 95 wt %.

In at least one embodiment, the isomerized product contains less than 70 wt % of di-substituted vinylidene, such as less than 40 wt %, such as less than 30 wt %, such as less than 20 wt %, such as less than 10 weight %, such as less than 5 wt %.

The isomerization conditions, such as temperature and pressure, can depend upon the feed stock employed and the desired pour point of the product produced. Isomerization can be performed at a temperature from about 150° C. to about 475° C. In at least one embodiment, isomerization is performed at a temperature from about 200° C. to about 450° C., such as from about 200° C. to about 270° C. The temperature can be controlled using one or more heat exchangers, such as a heat jacket, coupled with a line as the PAO intermediate flows through the line.

A pressure used for isomerization may be from about 0.07 MPa to about 13.8 MPa (1 psi to 2,000 psi). In at least one embodiment, the pressure is from about 0.07 MPa to about 6.89 MPa (10 psi to 1,000 psi), such as about 0.69 MPa to 4.14 MPa (100 psi to 600 psi).

The pressure used for isomerization can be controlled using flow rates of the PAO intermediate (as a first reactor effluent) through a line to a subsequent processing unit (such as a filtration unit or distillation unit). For example, a higher flow rate of PAO intermediate through a line promotes a higher pressure experienced by the PAO intermediate in the line, as compared to a lower flow rate through the line. In at least one embodiment, a flow rate of PAO intermediate through a line is from about 1 lb/min to about 5,000 lbs/min, such as from about 30 lbs/min to about 300 lbs/min.

The pressure and flow rate can be controlled using one or more pumps coupled with a line as the PAO intermediate flows through the line.

Filtration

The PAO intermediate or isomerized product can be transferred via a line to a filtration unit. It has been discovered that, in embodiments using an isomerized product, for example, the isomerized product can be filtered through a less expensive and less complex filtration unit instead of a conventional cellulosic body feed-type filtration unit, which provides additional cost savings and throughput enhancement. Cellulosic body feed-type filtration units can be those having a cellulosic body feed-type filter which has polar groups (e.g., hydroxyl groups) that couple with contaminants in the feed through the filtration unit.

Alternatively, in embodiments using an isomerized product, for example, a filtration unit is merely optional and the isomerized product can be transferred from the first reactor to a distillation unit or the second reactor. Because filtration can be bypassed completely, overall throughput enhancement of end products is achieved.

Filtration units of the present disclosure can include crude particulate filters, such as a particulate filter having a large pore size. Particulate filters can include a cartridge filter, a cellulosic cartridge filter, bag filter, or other filtration device, and/or can have an average pore size of from about 0.1 micron to about 100 microns.

Because filters having large pore sizes can be used, flow rates of isomerized product (or PAO intermediate) through filtration units of the present disclosure can be greater than flow rates used for conventional cellulosic body feed-type filtration units. Because flow rates of isomerized product (or PAO intermediate) through filtration units of the present disclosure can be greater than conventional flow rates, overall throughput enhancement of end products is achieved.

In at least one embodiment, a flow rate of isomerized product (or PAO intermediate) through a filtration unit is from about 1 lb/min to about 5,000 lbs/min, such as from about 10 lbs/min to about 300 lbs/min.

After filtration, a filtration effluent can be transferred to one or more distillation units and/or to a second reactor.

Distillation

In at least one embodiment, the intermediate PAO, isomerized product, and/or filtration effluent may be subjected to a distillation process to (1) remove water and other light byproducts and/or impurities, and (2) separate dimers (and unreacted alpha olefin monomers, if any) from the trimers and higher oligomers (if any). Any suitable distillation unit can be used for distillations of the present disclosure. In at least one embodiment, removal of water and other light byproducts and/or impurities is performed in a first distillation unit to form a first distillation effluent having dimers, trimers, and higher oligomers (if any). The first distillation effluent can be transferred to a second distillation unit for separation of dimers (and unreacted alpha olefin monomers, if any) from the trimers and higher oligomers (if any). The second distillation unit can form (1) a second distillation effluent having dimers (and unreacted alpha olefin monomers, if any) and (2) a third distillation effluent having trimers and higher oligomers (if any). The third distillation effluent can be transferred to a hydrogenation reactor, for example as described in more detail below. The second distillation effluent can be transferred to a second reactor (e.g., a second oligomerization reactor) and can optionally undergo an isomerization process before entering the second reactor. Performing an isomerization process on the second distillation effluent can be performed (1) in embodiments where a first isomerization process has not been performed (e.g., a first isomerization process described above) or (2) in addition to a first isomerization process of vinylidene dimers (e.g., as described above).

In at least one embodiment, a distillation unit is configured to remove water and other light byproducts and/or impurities from a feed. The distillation unit can be operated at a cut point of from about 50° C. to about 400° C. at a pressure of from about 0.1 mmHg to 760 mmHg, such as about 150° C. to about 275° C. at a pressure of from about 1 mmHg to about 50 mmHg.

In at least one embodiment, a distillation unit is configured to separate dimers (and unreacted alpha olefin monomers, if any) from trimers and higher oligomers (if any). The distillation unit can be operated at a cut point of from about 50° C. to about 400° C. at a pressure of from about 0.1 mmHg to 760 mmHg, such as about 200° C. to about 300° C. at a pressure of from about 1 mmHg to about 20 mmHg.

Second Isomerization

A distillation effluent having vinylidene dimers may be subjected to isomerization to form an isomerized product (e.g., a second isomerized product) comprising tri-substituted olefin dimers, e.g., tri-substituted vinylene dimers). A second isomerization can be performed instead of, or in addition to, a first isomerization of the intermediate PAO.

Distillation effluent can be, for example, a distillation effluent of a second distillation unit (e.g., as described above).

It has been discovered that vinylidene dimers (of a distillation effluent) can be isomerized in the absence of added isomerization catalyst, rendering isomerization in an additional reactor merely optional. Accordingly, a heat exchanger can be coupled with a line transporting the distillation effluent (comprising vinylidene dimers) from a distillation unit to a second reactor (e.g., a second oligomerization reactor). Isomerizing vinylidene dimers in the absence of added isomerization catalyst (and/or in the absence of an isomerization reactor) provides substantial cost savings and throughput enhancement, as compared to conventional poly alpha olefin processes. Without being bound by theory, it is believed that there may be one or more unidentified catalytic species present in the intermediate PAO and distillation effluent that can catalyze the isomerization reaction(s). If so, the catalytic species likely has/have a comparable boiling point as the boiling point of vinylidene dimers and/or tri-substituted olefin dimers.

In at least one embodiment, an isomerized product (e.g., a second isomerized product) contains greater than 50 wt %, such as greater than 55 wt %, such as greater than 60 wt %, such as greater than 65 wt %, such as greater than 75 wt %, such as greater than 85 wt %, such as greater than 90 wt %, such as greater than 95 wt % of tri-substituted vinylene dimer represented by the general structure above.

In at least one embodiment, an isomerized product (e.g., a second isomerized product) contains less than 70 wt %, such as less than 40 wt %, such as less than 30 wt %, such as less than 20 wt %, such as less than 10 weight %, such as less than 5 wt % of di-substituted vinylidene.

The isomerization conditions, such as temperature and pressure, can depend upon the feed stock employed and the desired pour point of the product produced. Isomerization can be performed at a temperature from about 150° C. to about 475° C. In at least one embodiment, isomerization is performed at a temperature from about 200° C. to about 450° C., such as from about 200° C. to about 270° C. The temperature can be controlled using one or more heat exchangers, such as a heat jacket, coupled with a line as the distillation effluent flows through the line.

A pressure used for isomerization may be from about 0.07 MPa to about 13.8 MPa (1 psi to 2,000 psi). In at least one embodiment, the pressure is from about 0.07 MPa to about 6.89 MPa (10 psi to 1,000 psi), such as about 0.69 MPa to 4.14 MPa (100 psi to 600 psi).

The pressure used for isomerization can be controlled using flow rates of the distillation effluent through a line to a subsequent processing unit (such as a second oligomerization reactor). For example, a higher flow rate of distillation effluent through a line promotes a higher pressure experienced by the distillation effluent in the line, as compared to a lower flow rate through the line. In at least one embodiment, a flow rate of distillation effluent through a line is from about 5 lbs/min to about 1,000 lbs/min, such as from about 10 lbs/min to about 300 lbs/min.

The pressure and flow rate can be controlled using one or more pumps coupled with a line as the distillation effluent flows through the line.

Second Oligomerization

The intermediate PAO from the first oligomerization (or a filtration effluent or a distillation effluent) may be used as the sole olefin feedstock to the subsequent oligomerization or may be used together with an alpha olefin feedstock of the type used as the olefin starting material for the first oligomerization. Other portions of the effluent from the first oligomerization may also be used as a feedstock to the subsequent oligomerization, including unreacted LAO. The intermediate PAO dimer may suitably be separated from the overall intermediate PAO product by distillation (e.g., as described above), with the cut point set at a value dependent upon the fraction to be used as lube base stock or the fraction to be used as feed for the subsequent oligomerization. Alpha olefins with the same attributes as those used for the first oligomerization may be used for the second oligomerization. Typically ratios for the intermediate PAO dimer fraction (or filtration effluent or distillation effluent) to the alpha olefins fraction in the feedstock are from about 90:10 to about 10:90, such as from about 80:20 to about 20:80 by weight. In at least one embodiment, the intermediate PAO dimer (or filtration effluent or distillation effluent) will make up around 50 mole % of the olefinic feed material since the properties and distribution of the final product, dependent in part upon the starting material, can be favorably affected by feeding the intermediate PAO dimer (or filtration effluent or distillation effluent) at an equimolar ratio with the alpha olefins. Temperatures for the subsequent oligomerization in the second reactor can be from about 15° C. to about 60° C.

Any suitable oligomerization process and catalyst may be used for the subsequent oligomerization. A catalyst for the subsequent oligomerization can be a non-transition metal catalyst. A catalyst can be a Lewis acid catalyst. Patent applications US 2009/156874 and US 2009/240012 describe a process for the subsequent oligomerization, to which reference is made for details of feedstocks, compositions, catalysts and co-catalysts, and process conditions. The Lewis acid catalysts of US 2009/156874 and US 2009/240012 include the metal and metalloid halides conventionally used as Friedel-Crafts catalysts, examples include $AlCl_3$, $BF_3$, $AlBr_3$, $TiCl_3$, and $TiCl_4$ either alone or with a protic promoter/activator. Boron trifluoride is commonly used but not particularly suitable unless it is used with a protic promoter. Useful co-catalysts are well known and described in detail in US 2009/156874 and US 2009/240012. Solid Lewis acid catalysts, such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates (e.g., $WO_x/ZrO_2$, $WO_x/MoO_3$) may also be used although these are not generally as favored economically. Additional process conditions and other details are described in detail in US 2009/156874 and US 2009/240012, and incorporated herein by reference.

In at least one embodiment, the subsequent oligomerization is performed in the presence of $BF_3$ and at least two different activators selected from alcohols and alkyl acetates. The alcohols are $C_1$ to $C_{10}$ alcohols and the alkyl acetates are $C_1$ to $C_{10}$ alkyl acetates. For example, both co-activators are $C_1$ to $C_6$ based compounds. Two example combinations of co-activators are i) ethanol and ethyl acetate and ii) n-butanol and n-butyl acetate. The ratio of alcohol to alkyl acetate can be from about 0.2 to about 15, such as from about 0.5 to about 7.

The structure of the intermediate PAO (or filtration effluent or distillation effluent) is such that, when reacted in a subsequent oligomerization, the intermediate PAO (or filtration effluent or distillation effluent) reacts preferentially with the optional LAO to form a co-dimer of the dimer and LAO at high yields. This allows for high conversion and yield rates of the PAO products. In at least one embodiment, the PAO product from the subsequent oligomerization comprises primarily a co-dimer (e.g., an trimer) formed from the dimer and the respective LAO feedstock. In at least one embodiment, where the LAO feedstock for both oligomerization processes is 1-decene, the incorporation of intermediate Cm PAO dimer into higher oligomers can be greater than about 80%, such as greater than about 90%, the conversion of the LAO can be greater than about 95%, such as greater than about 99%, and/or the yield % of $C_{30}$ product in the overall product mix can be greater than about 75%, such as greater than about 90%. In another embodiment, where the LAO feedstock is 1-octene, the incorporation of the intermediate PAO dimer into higher oligomers can be greater than about 80%, such as greater than about 90%, the conversion of the LAO can be greater than about 95%, such as greater than about 99%, and/or the yield % of $C_{28}$ product in the overall product mix can be greater than about 75%, such as greater than about 90%. In another embodiment, where the feedstock is 1-dodecene, the incorporation of the intermediate PAO dimer into higher oligomers can be greater than about 80%, such as greater than about 90%, the conversion of the LAO can be greater than about 95%, such as greater than about 99%, and/or the yield % of $C_{32}$ product in the overall product mix can be greater than about 75%, such as greater than about 90%.

In at least one embodiment, the monomer is optional as a feedstock in the second reactor. In some embodiments, the first reactor effluent comprises unreacted monomer, and the unreacted monomer is fed to the second reactor. In some embodiments, monomer is fed into the second reactor, and the monomer is an LAO selected from the group including 1-hexene, 1-octene, 1-nonene, 1-decene, 1-dodecene, and 1-tetradecene. In some embodiments, the PAO produced in the subsequent oligomerization is derived from the intermediate PAO dimer plus only one monomer. In some embodiments, the PAO produced in the subsequent oligomerization is derived from the intermediate PAO dimer plus two or more monomers, or three or more monomers, or four or more monomers, or even five or more monomers. For example, the intermediate PAO dimer plus a $C_8$, $C_{10}$, $C_{12}$-LAO mixture, or a $C_6$, $C_7$, $C_8$, $C_9$, $C_{10}$, $C_{11}$, $C_{12}$, $C_{13}$, $C_{14}$-LAO mixture, or a $C_4$, $C_6$, $C_8$, $C_{10}$, $C_{12}$, $C_{14}$, $C_{16}$, $C_{18}$-LAO mixture can be used as a feed. In some embodiments, the PAO produced in the subsequent oligomerization comprises less than 30 mole % of $C_2$, $C_3$ and $C_4$ monomers, such as less than 20 mole %, such as less than 10 mole %, such as less than 5 mole %, such as less than 3 mole %, such as 0 mole %. Specifically, in another embodiment, the PAO produced in the subsequent oligomerization comprises less than 30 mole % of ethylene, propylene and butene, such as less than 20 mole %, such as less than 10 mole %, such as less than 5 mole %, such as less than 3 mole %, such as 0 mole %.

The PAOs produced in the subsequent oligomerization may be a mixture of dimers, trimers, and optionally tetramer and higher oligomers. This PAO is referred to interchangeably as the "second reactor effluent." The properties of the isomerized product(s) of the present disclosure enable a high yield of a co-dimer (e.g., trimers) of tri-substituted vinylene dimers and LAO in the second reactor effluent. The PAOs in the second reactor effluent are especially notable because very low viscosity PAOs can be achieved at very high yields, and these PAOs can have excellent rheological properties, including low pour point, Noack volatility, and very high viscosity indexes.

In at least one embodiment, the PAOs of the second reactor effluent may contain trace amounts of transition metal compound if the catalyst in the first or subsequent oligomerization is a metallocene catalyst. A trace amount of transition metal compound may be any amount of transition metal compound or Group 4 metal present in the PAO. Presence of Group 4 metal may be detected at the ppm or ppb level by ASTM 5185.

The second reactor effluent PAO can have a portion having a carbon count of $C_{28}$-$C_{32}$, wherein the $C_{28}$-$C_{32}$ portion is at least about 65 wt %, such as at least about 70 wt %, such at least about 80 wt %, such as at least about 90 wt %, such as at least about 95 wt %, such as at least about 99 wt %, such as from about 70 wt % to about 99 wt %, such as from about 70 wt % to about 90 wt %, of the second reactor effluent.

The kinematic viscosity at 100° C. of the second reactor effluent PAO can be less than about 10 cSt, such as less than about 6 cSt, such as less than about 4.5 cSt, such as less than about 3.2 cSt, such as from about 2.8 to about 4.5 cSt. The kinematic viscosity at 100° C. of the C28 portion of the PAO can be less than 3.2 cSt. In at least one embodiment, the kinematic viscosity at 100° C. of the $C_{28}$ to $C_{32}$ portion of the second reactor effluent PAO can be less than about 10 cSt, such as less than about 6 cSt, such as less than about 4.5 cSt, such as from about 2.8 to about 4.5 cSt.

In at least one embodiment, the pour point of the PAO is below about −40° C., such as below about −50° C., such as below about −60° C., such as below about −70° C., such as below about −80° C. The pour point of the $C_{28}$ to $C_{32}$ portion of the second reactor effluent PAO can be below −30° C., such as below about −40° C., such as below about −50° C., such as below about −60° C., such as below about −70° C., such as below about −80° C.

The Noack volatility of the second reactor effluent PAO may be not more than about 9.0 wt %, such as not more than about 8.5 wt %, such as not more than about 8.0 wt %, such as not more than about 7.5 wt %. The Noack volatility of the $C_{28}$ to $C_{32}$ portion of the second reactor effluent PAO may be less than about 19 wt %, such as less than about 14 wt %, such as less than about 12 wt %, such as less than about 10 wt %, such as less than about 9 wt %.

The viscosity index of the second reactor effluent PAO can be more than about 121, such as more than about 125, such as more than about 130, such as more than about 136. The viscosity index of the trimer or $C_{28}$ to $C_{32}$ portion of the second reactor effluent PAO can be above about 120, such as above about 125, such as above about 130, such as at least about 135.

The cold crank simulator value (CCS) at −25° C. of the second reactor effluent PAO or a portion of the second reactor effluent PAO may be not more than about 500 cP, such as not more than about 450 cP, such as not more than about 350 cP, such as not more than about 250 cP, such as from about 200 to about 450 cP, such as about 100 to about 250 cP.

In at least one embodiment, the second reactor effluent PAO has a kinematic viscosity at 100° C. of not more than about 3.2 cSt and a Noack volatility of not more than about 19 wt %. In another embodiment, the second reactor effluent PAO has a kinematic viscosity at 100° C. of not more than about 4.1 cSt and a Noack volatility of not more than about 9 wt %.

The ability to achieve such low viscosity PAOs with such low Noack volatility at such high yields is noteworthy, and attributable to the high tri-substituted vinylene dimer content (provided by one or more isomerization processes) of various feeds of the processes of the present disclosure. The tri-substituted vinylene dimers have properties that make them selectively reactive in the subsequent oligomerization process.

Hydrogenation

The second reactor effluent PAO from the subsequent oligomerization can be hydrogenated prior to use as a lubricant basestock to remove any residual unsaturation and stabilize the product. An optional hydrogenation may be carried out in any suitable manner for hydrotreating conventional PAOs.

Hydrogenation may be performed in any suitable hydrogenation reactor. The catalyst employed in the isomerization reaction may saturate the second reactor effluent PAO.

Any conventional hydrogenation reaction may be employed in the present disclosure. For example, the hydrogenation process described in U.S. Pat. No. 4,125,569, which is incorporated herein by reference, may be employed. Hydrogenation catalysts include nickel on Kieselguhr catalyst and conventional metallic hydrogenation catalysts, for example, oxide, hydroxide, or free metal forms of the Group VIII metals, such as cobalt, nickel, palladium, and platinum. The metals can be associated with carriers such as bauxite, alumina, silica gel, silica-alumina composites, activated carbon, crystalline aluminosilicate zeolites, and clay. Also, non-noble Group VIII metals, metal oxides, and sulfides can be used. Additional examples of catalysts which may be employed in the hydrogenation reaction are disclosed in U.S. Pat. Nos. 3,852,207; 4,157,294; 3,904,513; and 4,673,487, which are incorporated herein by reference. The catalysts mentioned above may be employed separately or in combination with one another.

In the hydrogenation reaction, a slight excess to a large excess of hydrogen can be used. Unreacted hydrogen may be separated from the hydrogenated product and recycled to the hydrogenation reactor.

The hydrogenation reactor provides hydrogenated product effluent that can then be transferred to one or more distillation units to separate an ultra-low viscosity PAO (e.g., about 3 cST) from an intermediate viscosity PAO (e.g., about 6 cST) and any residual heavies present in the effluent.

Polyalphaolefin Product

The intermediate PAOs and PAOs produced (e.g., hydrogenated PAOs) by the processes of the present disclosure, particularly those of ultra-low viscosity, can be especially suitable for high performance automotive engine oil formulations either by themselves or by blending with other fluids, such as Group II, Group II+, Group III, Group III+ or lube basestocks derived from hydroisomerization of wax fractions from Fisher-Tropsch hydrocarbon synthesis from $CO/H_2$ syn gas, or other Group IV or Group V basestocks. They can be preferred grades for high performance industrial oil formulations that call for ultra-low and low viscosity oils. Additionally, they can be suitable for use in personal care applications, such as soaps, detergents, creams, lotions, shampoos, and detergents.

The PAO formed following hydrogenation ("hydrogenated PAO") may have a KV100 not greater than about 20 cSt. In at least one embodiment, the KV100 of the product can be from about 1 cSt to about 20 cSt, about 1.2 to about 15 cSt, about 1.5 to about 15 cSt, about 1.5 to about 10 cSt, about 3 to about 15 cSt, or about 3 to about 10 cSt. In some embodiments, the PAO has a KV100 of from about 1 to about 6, such as from about 1.2 to about 5, such as about 1.5 to about 5, such as about 3 to about 4. In some embodiments, the PAO has a maximum KV100 of 20, 18, 15, 10, or 8.

The hydrogenated PAOs can have a pour point of less than about −20° C. In some embodiments, the pour point is less than about −40° C., less than about −55° C., or less than about −60° C.

In at least one embodiment, the hydrogenated PAOs have a VI above about 100, such as above about 110, such as above about 120, such as above about 130, such as above about 140, such as above about 150. In at least one embodiment, the VI is from about 120 to about 145, such as about 120 to about 155, or about 120 to about 160.

Hydrogenated PAOs can have a KV100 of about 3 cSt or less with low pour points, which can be useful in the formulation of specialty, fuel/energy efficient transmission or hydraulic fluids. The low viscosity fluids having a KV100 of about 3 cSt may be useful as high performance fuel and/or energy efficient base stocks.

Examples of Configurations

Figure 1:
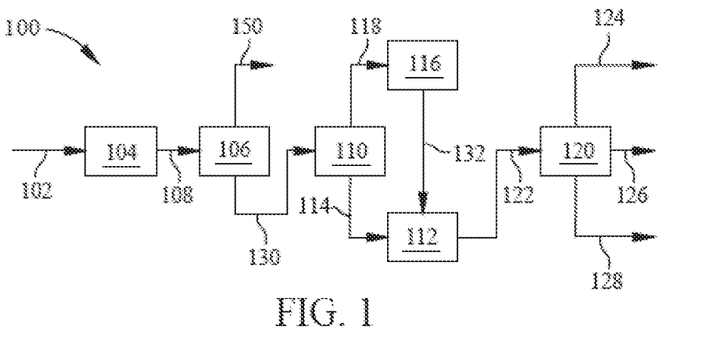
FIG. 1 is an apparatus for forming poly alpha olefins, according to at least one embodiment.

FIG. 1 is a diagram illustrating an apparatus for carrying out certain aspects of the present disclosure according to at least one embodiment. More generally, a configuration shown in FIG. 1 or similar to FIG. 1 can be used for forming poly alpha olefins of the present disclosure.

As shown in FIG. 1, an apparatus 100 includes a feed line 102 coupled with a first reactor 104 (e.g., an oligomerization reactor). During use, a feed of feed line 102 can include an alpha olefin. First reactor 104 is coupled with a first distillation unit 106 via line 108. A first reactor effluent (including intermediate PAO) of line 108 is transferred to first distillation unit 106 where byproducts and/or contaminants can be separated from the first reactor effluent. The byproducts and/or contaminants may be removed, typically as a tops fraction 150. First distillation unit 106 is coupled with a second distillation unit 110 via line 130. A first distillation effluent (including intermediate PAO) of line 130 is transferred to second distillation unit 110. Second distillation unit 110 is coupled with a second reactor 116 (e.g., an oligomerization reactor) via line 118. A distillation effluent including dimers and unreacted monomers of line 118 is transferred to second reactor 116. Second distillation unit 110 is further coupled with a hydrogenation reactor 112 via line 114. A distillation effluent including trimers, tetramers, and higher oligomers (if any) of line 114 is transferred to the hydrogenation reactor 112. Second reactor 116 is coupled with the hydrogenation reactor 112 via line 132. An effluent of the second reactor (e.g., effluent including trimers) of line 132 is transferred to hydrogenation reactor 112. Alternatively, second reactor 116 can be coupled with a separate hydrogenation reactor (not shown) (e.g., not reactor 112). As shown in FIG. 1, hydrogenation reactor 112 is coupled with a third distillation unit 120 via line 122. A hydrogenated PAO product of line 122 is transferred to the third distillation unit 120 for separation into an ultra-low viscosity PAO (trimer) (removed by effluent line 126), a low to medium viscosity PAO (tetramer+) (removed by effluent line 128), and a lights fraction (dimer or lighter) (removed by effluent line 124).

Figure 2:
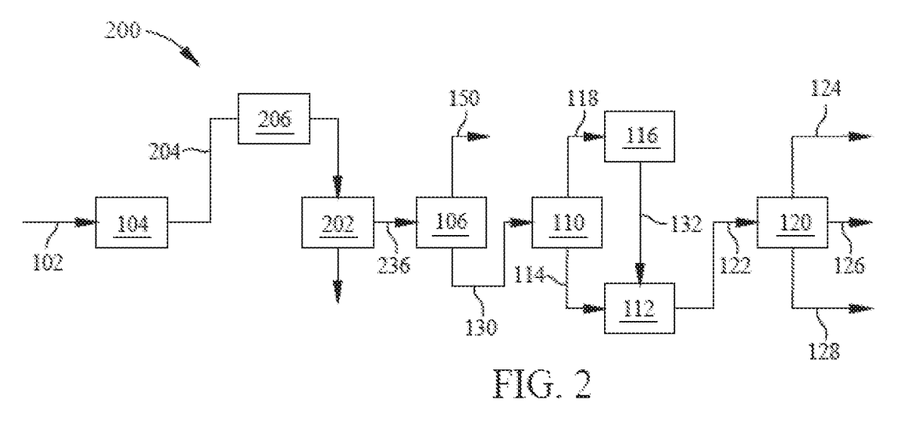
FIG. 2 is an apparatus for forming poly alpha olefins, according to at least one embodiment.

FIG. 2 is a diagram illustrating an apparatus for carrying out certain aspects of the present disclosure. More generally, a configuration shown in FIG. 2 or similar to FIG. 2 can be used for forming poly alpha olefins of the present disclosure.

As shown in FIG. 2, an apparatus 200 includes a feed line 102 coupled with a first reactor 104 (e.g., an oligomerization reactor). During use, a feed of feed line 102 can include an alpha olefin. First reactor 104 is coupled with filtration unit 202 via line 204. A heat exchanger 206 is coupled with line 204 to provide heat to the first reactor effluent of line 204 and increase the tri-substituted vinylene dimer content of the first reactor effluent. The first reactor effluent (including intermediate PAO) of line 204 having increased tri-substituted vinylene dimer content is transferred to filtration unit 202 where particulates (if any) are filtered using a filter (e.g., a large-pore filter). Filtration unit 202 is coupled with a first distillation unit 106 via line 236. A filtration effluent (including intermediate PAO) of line 236 is transferred to first distillation unit 106 where byproducts and/or contaminants can be separated from the first reactor effluent, typically as a tops fraction 150. The first distillation unit 106 is coupled with a second distillation unit 110 via a line 130. A first distillation effluent (including intermediate PAO) flowing through the line 130 can be transferred to the second distillation unit 110. Second distillation unit 110 is coupled with a second reactor 116 (e.g., an oligomerization reactor) via line 118. A distillation effluent including dimers and unreacted monomers of line 118 is transferred to second reactor 116. Second distillation unit 110 is further coupled with a hydrogenation reactor 112 via line 114. A distillation effluent including trimers, tetramers, and higher oligomers (if any) of line 114 is transferred to the hydrogenation reactor 112. Second reactor 116 is coupled with the hydrogenation reactor 112 via line 132. An effluent of the second reactor (e.g., effluent including trimers) of line 132 is transferred to hydrogenation reactor 112. Alternatively, second reactor 116 can be coupled with a separate hydrogenation reactor (not shown) (e.g., not reactor 112). As shown in FIG. 1, hydrogenation reactor 112 is coupled with a third distillation unit 120 via line 122. A hydrogenated PAO product of line 122 is transferred to the third distillation unit 120 for separation into an ultra-low viscosity PAO (trimer) (removed by effluent line 126), a low to medium viscosity PAO (tetramer+) (removed by effluent line 128), and a lights fraction (dimer or lighter) (removed by effluent line 124).

Figure 3:
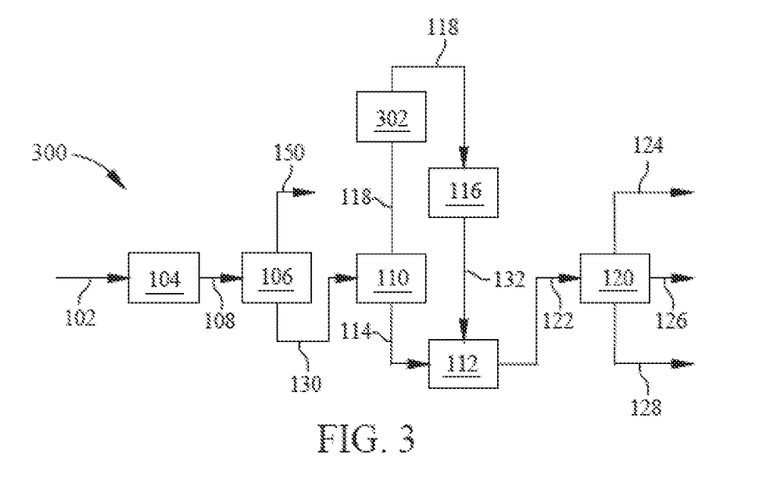
FIG. 3 is an apparatus for forming poly alpha olefins, according to at least one embodiment.

FIG. 3 is a diagram illustrating an apparatus for carrying out certain aspects of the present disclosure. More generally, a configuration shown in FIG. 3 or similar to FIG. 3 can be used for forming poly alpha olefins of the present disclosure.

As shown in FIG. 3, an apparatus 300 includes a feed line 102 coupled with a first reactor 104 (e.g., an oligomerization reactor). During use, a feed of feed line 102 can include an alpha olefin. First reactor 104 is coupled with a first distillation unit 106 via line 108. A first reactor effluent (including intermediate PAO) of line 108 is transferred to first distillation unit 106 where byproducts and/or contaminants can be separated from the first reactor effluent, typically as a tops fraction 150. First distillation unit 106 is coupled with a second distillation unit 110 via line 130. A first distillation effluent (including intermediate PAO) of line 130 is transferred to second distillation unit 110. Second distillation unit 110 is coupled with a second reactor 116 (e.g., an oligomerization reactor) via line 118. A distillation effluent including dimers and unreacted monomers of line 118 is transferred to second reactor 116. A heat exchanger 302 is coupled with line 118 to provide heat to the distillation effluent and increase the tri-substituted vinylene dimer content of the distillation effluent that is then transferred to second reactor 116. Second distillation unit 110 is further coupled with a hydrogenation reactor 112 via line 114. A distillation effluent including trimers, tetramers, and higher oligomers (if any) of line 114 is transferred to the hydrogenation reactor 112. Second reactor 116 is coupled with the hydrogenation reactor 112 via line 132. An effluent of the second reactor (e.g., effluent including trimers) of line 132 is transferred to hydrogenation reactor 112. Alternatively, second reactor 116 can be coupled with a separate hydrogenation reactor (not shown) (e.g., not reactor 112). As shown in FIG. 1, hydrogenation reactor 112 is coupled with a third distillation unit 120 via line 122. A hydrogenated PAO product of line 122 is transferred to the third distillation unit 120 for separation into an ultra-low viscosity PAO (trimer) (removed by effluent line 126), a low to medium viscosity PAO (tetramer+) (removed by effluent line 128), and a lights fraction (dimer or lighter) (removed by effluent line 124).

EMBODIMENTS LISTING

The present disclosure provides, among others, the following embodiments, each of which may be considered as optionally including any alternate embodiments.

Clause 1. A process to produce a poly alpha olefin, the process comprising:

introducing a first olefin monomer to a first catalyst and an activator in a first reactor to form a first reactor effluent comprising olefin dimers and olefin trimers;

heating the first reactor effluent to form an isomerized product;

introducing the isomerized product to a filtration unit to form a filtration effluent;

introducing the filtration effluent to a first distillation unit to form a first distillation effluent;

optionally introducing the first distillation effluent to a second distillation unit to form a second distillation effluent; and introducing the first distillation effluent and/or the second distillation effluent to a second catalyst in a second reactor to form a second reactor effluent comprising the olefin trimers.

Clause 2. The process of Clause 1, further comprising introducing the second reactor effluent to a third reactor and hydrogenating the second reactor effluent to form a hydrogenated effluent.

Clause 3. The process of Clauses 1 or 2, further comprising transferring the hydrogenated effluent to a third distillation unit to form an ultra-low viscosity poly alpha olefin effluent.

Clause 4. The process of any of Clauses 1 to 3, wherein the first catalyst is a metallocene catalyst and the second catalyst is $BF_3$.

Clause 5. The process of any of Clauses 1 to 4, wherein heating comprises providing heat to a line comprising the first reactor effluent via one or more heat exchangers.

Clause 6. The process of any of Clauses 1 to 5, wherein the isomerized product comprises greater than 85 wt % of tri-substituted vinylene dimer.

Clause 7. The process of any of Clauses 1 to 6, wherein the isomerized product comprises greater than 95 wt % of tri-substituted vinylene dimer.

Clause 8. The process of any of Clauses 1 to 7, wherein heating is performed at a temperature of about 200° C. or greater, such as 230° C. or greater.

Clause 9. The process of any of Clauses 1 to 8, wherein heating is performed at a pressure of about 100 psi to about 600 psi.

Clause 10. The process of any of Clauses 1 to 9, wherein introducing the isomerized product to the filtration unit comprises introducing the isomerized product to a particulate filter having an average pore size of from about 5 to about 20.

Clause 11. The process of any of Clauses 1 to 10, wherein introducing the isomerized product to the filtration unit comprises flowing the isomerized product through the filtration unit at a rate of from about 10 lbs/min. to about 300 lbs/min.

Clause 12. A process to produce a poly alpha olefin, the process comprising:

introducing a first olefin monomer to a first catalyst and an activator in a first reactor to form a first reactor effluent comprising olefin dimers and olefin trimers;

introducing the first reactor effluent to a first distillation unit to form a first distillation effluent;

optionally introducing the first distillation effluent to a second distillation unit to form a second distillation effluent;

heating the first distillation effluent and/or second distillation effluent to form an isomerized product; and introducing the isomerized product to a second catalyst in a second reactor to form a second reactor effluent comprising the olefin trimers.

Clause 13. The process of Clause 12, further comprising introducing the second reactor effluent to a third reactor and hydrogenating the second reactor effluent to form a hydrogenated effluent.

Clause 14. The process of Clauses 12 or 13, further comprising transferring the hydrogenated effluent to a third distillation unit to form an ultra-low viscosity poly alpha olefin effluent.

Clause 15. The process of any of Clauses 12 to 14, wherein the first catalyst is a metallocene catalyst and the second catalyst is a Lewis acid, such as $BF_3$ or $AlCl_3$.

Clause 16. The process of any of Clauses 12 to 15, wherein heating comprises providing heat to a line comprising the first distillation effluent via one or more heat exchangers.

Clause 17. The process of any of Clauses 12 to 16, wherein the isomerized product comprises greater than 85 wt % of tri-substituted vinylene dimer.

Clause 18. The process of any of Clauses 12 to 17, wherein the isomerized product comprises greater than 95 wt % of tri-substituted vinylene dimer.

Clause 19. The process of any of Clauses 12 to 18, wherein heating is performed at a temperature of about 200° C. or greater, such as 230° C. or greater.

Clause 20. The process of any of Clauses 12 to 19, wherein heating is performed at a pressure of about 10 psi to about 600 psi.

Clause 21. A process to produce a poly alpha olefin, the process comprising:

introducing a first olefin monomer to a first catalyst and an activator in a first reactor to form a first reactor effluent comprising olefin dimers and olefin trimers;

introducing the first reactor effluent to a first distillation unit to form a first distillation effluent;

introducing the first distillation effluent to a second distillation unit to form a second distillation effluent; and introducing the second distillation effluent to a second catalyst in a second reactor to form a second reactor effluent comprising the olefin trimers.

Clause 22. The process of Clause 21, further comprising introducing the second reactor effluent to a third reactor and hydrogenating the second reactor effluent to form a hydrogenated effluent.

Clause 23. The process of Clauses 21 or 22, further comprising transferring the hydrogenated effluent to a third distillation unit to form an ultra-low viscosity poly alpha olefin effluent.

Clause 24. The process of any of Clauses 21 to 23, wherein the first catalyst is a metallocene catalyst and the second catalyst is $BF_3$.

Clause 25. An apparatus comprising:

a first reactor coupled at a first end with a first end of a first distillation unit;

a second distillation unit coupled with:
  a second end of the first distillation unit at a first end of the second distillation unit,
  a first end of a second reactor at a second end of the second distillation unit via a line, and
  a first end of a hydrogenation unit at a third end of the second distillation unit.

Clause 26. The apparatus of Clause 25, further comprising a heat exchanger coupled with the line.

Clause 27. The apparatus of Clauses 25 or 26, further comprising a third distillation unit coupled at a first end with a second end of the hydrogenation unit.

Clause 28. The apparatus of any of Clauses 25 to 27, wherein the second reactor is coupled with the hydrogenation unit.

Clause 29. An apparatus comprising:

a first reactor coupled at a first end with a first end of a filtration unit via a first line;

a first distillation unit coupled at a first end with a second end of the filtration unit;
a second distillation unit coupled with:
a second end of the first distillation unit at a first end of the second distillation unit,
a first end of a second reactor at a second end of the second distillation unit via a second line, and
a first end of a hydrogenation unit at a third end of the second distillation unit.

Clause 30. The apparatus of Clause 29, further comprising a heat exchanger coupled with the first line and/or the second line.

Clause 31. The apparatus of Clauses 29 or 30, further comprising a third distillation unit coupled at a first end with a second end of the hydrogenation unit.

Clause 32. The apparatus of any of Clauses 29 to 31, wherein the second reactor is coupled with the hydrogenation unit.

EXAMPLES

Experimental

Figure 4:
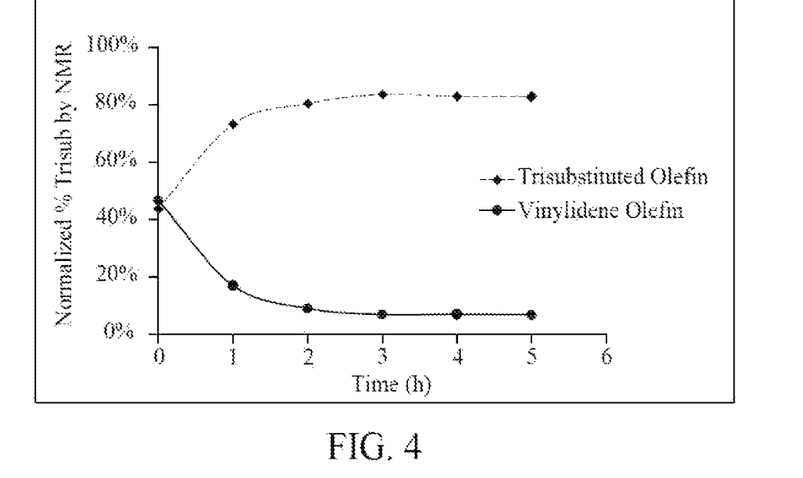
FIG. 4 is a graph illustrating normalized % tri-substituted vinylene dimers versus time, according to at least one embodiment.

Example 1: Both dimer samples were generated from dimerization of 1-decene using dimethylsilylbis(4,5,6,7-tetrahydroindenyl) zirconium dimethyl,N,N-dimethylanilinium tetrakis (pentafluorophenyl) borate and tri n-octyl aluminum (TNOA) as the catalyst/activator system. The sample was then distilled without addition of body feed or filtration to generate >98% dimer. An initial NMR was taken to confirm the distribution of vinylidene to trisubstituted olefin. The sample was then heated to 270° C. under nitrogen while stirring for over 22 hours and multiple samples were removed from the pot. All samples were analyzed by NMR, and the resulting ratios of trisubstituted olefin to vinylidene olefin are reported in FIG. 4. The initial ratio of trisubstituted olefin to vinylidene olefin is approximately 1:1 but significant isomerization of the olefin to the trisubstituted olefin occurs within 2 hours to give a ratio of 9:1.

Figure 5:
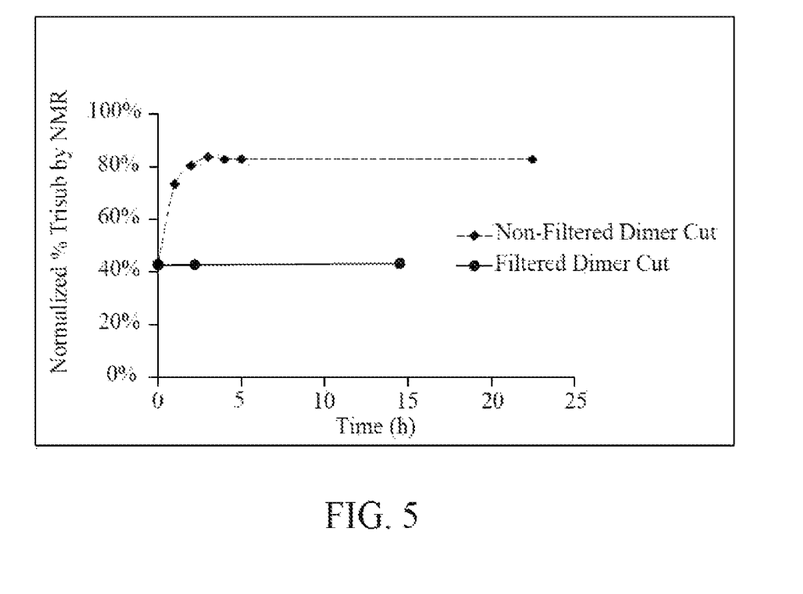
FIG. 5 is a graph illustrating normalized % tri-substituted vinylene dimers versus time, according to at least one embodiment.

Example 2: In a filtered sample, cellulosic body feed was added and the slurry was filtered to remove all polar components. The sample was then distilled to generate >98% dimer. An initial NMR was taken to confirm the distribution of vinylidene to trisubstituted olefin. The sample was then heated to 270° C. under nitrogen while stirring for over 14 hours and multiple samples were removed from the pot. All samples were analyzed by NMR. The comparison of trisubstituted dimer over analogous reaction times is shown in FIG. 5. FIG. 5 illustrates that the dimer sample generated from bypassing filtration results in significant isomerization to generate higher trisubstituted olefin. FIG. 5 further indicates that a dimer sample that has undergone filtration prior to isomerization exhibits no change in the amount of trisubstituted olefin.

Example 3: Dimer product from Example 1 was combined with 0.7 wt % Amberlyst 15 catalyst, and heated under nitrogen while stirring to 100° C. for over 22 hours. An NMR spectrum confirmed the distribution of vinylidene to trisubstituted vinylene olefin as ~1:1. After 22 hours, the ratio was 1:29 vinylidene to trisubstituted vinylene olefin by NMR. Filtration removes a key species that participates in isomerizing the vinylidene olefin to trisubstituted olefin. Reintroduction of a Lewis acid species, such as and Amberlyst catalyst, allows isomerization to occur to form predominantly the trisubstituted vinylene olefin.

Overall, the present disclosure provides processes and apparatuses for forming poly alpha olefins by isomerizing feeds to form feeds having high tri-substituted olefin dimer content. Isomerization of vinylidene dimers to tri-substituted olefin dimers provides higher overall yields of trimers. It has been discovered that vinylidene dimers can be isomerized in the absence of an added isomerization catalyst, rendering isomerization in an additional reactor merely optional. Isomerizing vinylidene dimers in the absence of an added isomerization catalyst (and/or in the absence of an isomerization reactor) provides substantial cost savings and throughput enhancement as compared to conventional poly alpha olefin processes. Furthermore, isomerizing vinylidene dimers in the absence of an added isomerization catalyst renders merely optional a filtration unit coupled with the first reactor. Additionally or alternatively, a less expensive and less complex filtration unit can be used (such as a crude particulate filter having a large pore size) instead of a conventional filtration unit, which provides additional cost savings and throughput enhancement.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and or testing procedures to the extent they are not inconsistent with this text.

As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A process to produce a poly alpha olefin, the process comprising:

introducing a first olefin monomer to a first catalyst, wherein the first catalyst is a metallocene catalyst, and an activator in a first reactor to form effluent comprising a vinylidene dimer;

heating the effluent to isomerize the vinylidene dimers to form tri-substituted olefin dimers to form an isomerized product;

introducing the isomerized product and a second olefin monomer to a second catalyst, wherein the second catalyst comprises a metal halide or metalloid halide, in a second reactor to form a second reactor effluent comprising olefin trimer formed by an oligomerization of the tri-substituted olefin dimers and the second olefin monomer.

2. The process of claim 1, wherein heating the effluent to isomerize the vinylidene dimers is performed without added isomerization catalysts.

3. The process of claim 1, wherein the second olefin monomer is the same as the first olefin monomer.

4. The process of claim 1, wherein the second olefin monomer is different from the first olefin monomer.

5. The process of claim 1, further comprising introducing the effluent to a distillation unit to form a distillation effluent; and wherein heating the effluent to isomerize the vinylidene dimers comprises heating one or more of a line connecting the first reactor and the distillation unit and a line connecting the distillation unit and the second reactor.

6. The process of claim 1, wherein the Lewis acid metal halide or metalloid halide is $BF_3$.

7. The process of claim 5, wherein the effluent is heated a temperature of about 200° C. or greater through the use of one or more heat exchangers.

8. The process of claim 1, wherein the isomerized product comprises greater than 85 wt % of tri-substituted vinylene dimer.

9. The process of claim 1, further comprising introducing the isomerized product to filtration unit having an average pore size of from about 5 to about 20 microns.

10. The process of claim 8, wherein the isomerized product comprises greater than 95 wt % of tri-substituted vinylene dimer.

11. The process of claim 5, wherein the line connecting the first reactor and the distillation unit is coupled to a heat exchanger.

12. The process of claim 5, wherein the line connecting the distillation unit and the second reactor is coupled to a heat exchanger.

13. The process of claim 1, wherein heating the effluent comprises heating the effluent along a line fluidly coupling the first reactor to a distillation unit upstream of the second reactor.

14. The process of claim 1, further comprising introducing the isomerized product and the second olefin monomer to the second catalyst and at least first and second co-activators.

15. The process of claim 14, wherein the first co-activator comprises an alcohol and the second co-activator comprises an alkyl acetate.

16. The process of claim 14, wherein the first co-activator comprises n-butanol and the second co-activator comprises n-butyl acetate.

17. The process of claim 1, wherein heating the effluent to isomerize the vinylidene dimers consists of heating only the effluent.

* * * * *